United States Patent [19]

Leipold

[11] Patent Number: 4,485,089

[45] Date of Patent: Nov. 27, 1984

[54] GEL TOOTHPASTES

[75] Inventor: Dianne P. Leipold, Newark, Del.

[73] Assignee: Hercules Incorporated, Wilmington, Del.

[21] Appl. No.: 542,911

[22] Filed: Oct. 17, 1983

[51] Int. Cl.³ .............................................. A61K 7/16
[52] U.S. Cl. ..................................................... 424/49
[58] Field of Search ................................... 424/49-58

[56] References Cited

U.S. PATENT DOCUMENTS

| 3,934,000 | 1/1976 | Barth | 424/49 |
| 4,314,990 | 2/1982 | Denny et al. | 424/52 |
| 4,357,313 | 11/1982 | Harvey et al. | 424/49 |

Primary Examiner—Shep K. Rose
Attorney, Agent, or Firm—Joanne L. Horn

[57] ABSTRACT

Disclosed are transparent dentifrice compositions comprising a humectant, a vehicle for the humectant, a finely divided dental abrasive, a silica thickener, and a hydrophobically modified hydroxyethyl cellulose thickening and gelling agent.

10 Claims, No Drawings

GEL TOOTHPASTES

The present invention relates to a transparent dentifrice composition comprising a humectant, a vehicle for the humectant, a finely divided dental abrasive, a silica thickener, and a hydrophobically modified hydroxyethyl cellulose thickener and gelling agent. Such dentifrice compositions are commonly referred to as toothpastes, in particular gel toothpastes.

Up until around 1970 the most common form of toothpaste was an opaque cream containing insoluble inorganic salts, such as dicalcium phosphate dihydrate, calcium pyrophosphate, and calcium carbonate, as the abrasive. While the abrasives are not necessary to remove plaque since simple brushing accomplishes that, they are used to remove stains from the teeth. Typically, the humectant to water ratio in cream toothpastes is 1:1. The thickener of choice in these cream systems is sodium carboxymethyl cellulose (CMC).

In the early '70s silica xerogels having an average particle size of approximately 8 to 9 microns were introduced as abrasives, and silica aerogels having an average particle size of approximately 4 microns were introduced as thickening agents for toothpastes, particularly gel toothpastes. Basically, the silica xerogels are able to provide the necessary abrasiveness since they do not hydrate in the presence of water. Silica aerogels, on the other hand, hydrate and swell in the presence of water which thereby accounts for their ability to thicken. The typical abrasive agents used in the cream toothpastes are not as abrasive as the silica xerogels used in the gel toothpaste. Hence, a lower concentration of the more abrasive silica xerogels can be used in the gel toothpastes, thereby allowing for the formation of a high humectant, low water, transparent gel toothpastes. Typically the humectant to water ratio in gel toothpastes is about 3.5:1.0. CMC is commonly used in gel toothpastes, but not as a thickening agent, rather as a rheological modifier and as a water binder.

Gel toothpastes are partially broken down or deformed during the extrusion of the gel from the tube onto the toothbrush. As a result, the toothpaste does not break cleanly from the orifice or nozzle end of the tube upon extrusion and tends to flatten and sink into the bristles of the toothbrush. In the past, polyethylene glycol has been added to overcome these deficiences (see e.g., U.S. Pat. No. 3,934,000). Gel toothpastes containing polyethylene glycol generally have a yield value of about 3000 to 4000 dyne/cm$^2$ at a shear rate of about 1.8 to 2.1 sec$^{-1}$. Generally the higher yield values are attained when heat is used in the manufacture of the toothpastes. However, even after the inclusion of polyethylene glycol, the gel toothpastes still have a stringier texture than is desirable upon extrusion from the tube, and exhibit some ribbon deformation after extrusion.

This invention provides a transparent dentifrice composition or gel toothpaste containing a hydrophobically modified hydroxyethyl cellulose alone or in combination with polyethylene glycol. The compositions of this invention have good body retention both during and after extrusion from the tube, and break from the tube with very little stringiness. Moreover, the compositions of this invention permit the empty tubes to be readily filled and retain good body character during storage.

The hydrophobically modified hydroxyethyl cellulose used in the compositions of this invention is further substituted with a hydrocarbon radical having from 8 to 25 carbon atoms, preferably from 12 to 20 carbon atoms, in an amount, by weight, from about 0.1% to about 0.9%, preferably from about 0.1% to about 0.7%. Suitably the hydrophobically modified hydroxyethyl cellulose is employed in an amount from about 0.1% to about 0.4%, preferably 0.2% to about 0.3%.

The term "hydrocarbon radical" as used herein is meant to include the hydrocarbon portion as well as any other moiety present, such as an ester, ether, or urethane moiety, as a result of the particular compound used to further substitute the hydroxyethyl cellulose.

The hydroxyethyl cellulose to be modified is typically of low to medium molecular weight, i.e., less than about 800,000, preferably 20,000 to about 500,000, and has a hydroxyethyl M.S. of from about 2.5 to about 3.5. The designation M.S. refers to the average number of moles of hydroxyethyl substituent groups combined per cellulosic anhydroglucose unit of the cellulose molecule. High molecular weight hydroxyethyl celluloses can also be hydrophobically modified and then degraded or depolymerized by any conventional means of degradation, such as treatment with peroxide, to obtain the desired molecular weight.

The hydrophobically modified hydroxyethyl cellulose can be prepared by the method set forth in U.S. Pat. No. 4,228,277.

The hydroxyethyl cellulose can be prepared by any known method, such as by treating a cellulose furnish with ethylene oxide in an alkaline medium. The cellulose furnish can be wood pulp or chemical cotton.

The hydrophobically modified hydroxyethyl cellulose can be combined with a polyethylene glycol having an average molecular weight from about 300 to about 20,000, preferably from about 300 to about 8000. Typically the polyethylene glycol is present in an amount from about 1% to about 5%, preferably from about 1% to about 3%. Polyethylene glycols and the methods of preparing same are well known in the art.

The finely divided dental abrasive is typically a high silica (SiO$_2$) content material preferably at least 70% SiO$_2$ having a particle size from about 2 to about 20 microns, and a refractive index which is substantially the same as the humectant. Generally the abrasive content in the compositions of this invention is from about 5% to about 50%, preferably from about 10% to about 30%. Suitable dental abrasive include amorphous silicic anhydrides having a particle size in the range set forth above, a surface area of at least 200 m$^2$/g, and a bulk density of at least 0.15 g/cm$^3$, such as, for example dehydrated silica hydrogels known as xerogels. Precipitated silicas or alkaline earth metal aluminosilicates, such as sodium aluminosilicate, having the same particle size range, surface area and bulk density as the silicic anhydrides can also be used as the dental abrasive.

The silica thickener can be a silica aerogel having an average particle size of about 4 microns, or a dehydrated silica hydrogel having a bulk density of less than 0.13 g/cm$^3$. Precipitated silicas and pyrogenic silicas having the same average particle size as the silica aerogels can also be used. Desirably the silica thickener is present in an amount from about 1% to about 10%, preferable 3% to 7%.

Typical humectants include glycerin, sorbitol, propylene glycol or mixtures thereof which are admixed with a suitable humectant vehicle, such as water. Humectants are used to retain moisture in the toothpaste, particularly at the nozzle end of the tube where the toothpaste can be in prolonged contact with the air. Typically the humectant and vehicle mixture contains from about 80% to about 90% humectant and from about 20% to about 10% vehicle.

Other conventional materials can be included in the compositions of this invention. For example, anionic, cationic, nonionic, and ampholytic surfactants, especially anionic surfactants having detergent and foaming properties; coloring agents; whitening agents; flavoring agents; sweetening agents; preservatives; antibacterial agents; and chlorophyll-containing compounds. Any of these additives can be present in the toothpaste of this invention in an amount up to about 5%. Typical anionic surfactants include sodium lauryl sulfate and sodium n-lauroyl sarcosinate and typical nonionic surfactants include block copolymers of ethylene oxide and propylene oxide wherein the ratio of ethylene oxide units to propylene oxide units is 2:1. Suitable flavoring agents include oils of peppermint, spearmint, and cinnamon. Sweetening agents, such as sodium saccharin; preservatives, such as sodium benzoate; and antibacterial agents, such as para-chlorophenyl biguanide, 4-chlorobenzyl-hydryl biguanide, and 5,6-dichloro-2-guanidinobenzimidazole also can be included in the compositions of this invention.

In addition, the compositions of this invention can contain a fluorine-containing compound in an amount sufficient to provide up to 1000 ppm fluoride ion content. Typical fluorine-containing compounds include sodium fluoride or sodium monofluorophosphate.

To further illustrate this invention, various illustrative examples are set forth below.

All parts and percentages are by weight, unless otherwise specified throughout this specification.

EXAMPLE 1

This example illustrates an embodiment of the composition of this invention and how to prepare it.

A mixing vessel equipped with a stirrer is charged with 3.06% water, 25.48% glycerin, 43.63% sorbitol solution (70% sorbitol in 30% water), 3.06% of polyethylene glycol having a molecular weight of about 600, and 0.31% hydrophobically modified hydroxyethyl cellulose having a hydroxyethyl M.S. of 3.5 and 0.64% of a $C_{16}$ hydrocarbon substitution. The contents of the vessel are mixed at 20 inches of vacuum at 25° C. until a homogeneous blend is obtained (about 30 minutes). The vessel is then charged with 0.19% sodium saccharin, 0.51% sodium benzoate, 0.78% sodium monofluorophosphate, and the contents of the vessel are mixed until a homogeneous blend is obtained (about 2 minutes). A silica xerogel having an average particle size of 8 microns, a surface area of about 320 m²/g and a bulk density of about 0.26 g/cm³ is added, and the contents of the vessel are mixed at 12 to 14 inches of vacuum for about 5 minutes until a homogeneous blend is obtained. The vessel is then charged with a silica aerogel (5.1%) having an average particle size of approximately 4 microns and a bulk density of about 0.11 g/cm³. The contents of the vessel are mixed at 12 to 14 inches of vacuum for about 5 minutes until a homogeneous blend is obtained. A peppermint flavoring agent (0.56%), a blue coloring agent (0.02%) and sodium lauryl sulfate (1.02%) are then added to the vessel, and the contents are stirred slowly at 26 inches of vacuum for about 30 minutes until a homogeneous blend is obtained. The resulting toothpaste has a yield value of 4500 dyne/cm² at a shear rate of 2.3 sec$^{-1}$, excellent body characteristics, and very short texture, i.e. little stringiness upon breaking from the tube after extrusion.

EXAMPLE 2

This example illustrates another embodiment of the composition of this invention.

The formulation and procedure of Example 1 are used except that all mixing or stirring is done at 35° C. instead of 25° C. The resulting toothpaste has a yield value of 4400 dyne/cm² at a shear rate of 3.6 sec$^{-1}$, excellent body characteristics, and short texture.

EXAMPLE 3

This example illustrates another embodiment of the composition of this invention.

The formulation and procedure of Example 1 are used except that no polyethylene glycol is added. The resulting toothpaste has a yield value of 2300 dyne/cm² at a shear rate of 2.5 sec$^{-1}$, good body characteristics and short texture.

EXAMPLE 4

This example illustrates another embodiment of the composition of this invention.

The formulation and procedure of Example 1 are used except that no polyethylene glycol is added and all mixing or stirring is conducted at 35° C. The resulting toothpaste has a yield value of 3000 dyne/cm² at a shear rate of 2.3 sec$^{-1}$, good body characteristics, and short texture.

EXAMPLE 5

This example illustrates another embodiment of the composition of this invention.

The formulation and procedure of Example 1 are used except that the hydrophobically modified hydroxyethyl cellulose used has a hydroxyethyl M.S. of 2.9, and 0.1% of a $C_{16}$ hydrocarbon radical substitution. The resulting toothpaste has a yield value of 3900 dyne/cm² at a shear rate of 2.7 sec$^{-1}$, excellent body characteristics, and short texture.

EXAMPLE 6

This example illustrates another embodiment of the composition of this invention.

The formulation and procedure of Example 1 are used except that the hydrophobically modified hydroxyethyl cellulose used has a hydroxyethyl M.S. of 3.3, and 0.4% of a $C_{16}$ hydrocarbon radical substitution. The resulting toothpaste has a yield value of 3400 dyne/cm² at a shear rate of 1.6 sec$^{-1}$, good body characteristics, and short texture.

EXAMPLE 7

This example illustrates another embodiment of this invention.

The formulation and procedure of Example 1 are used except that the hyphobically modified hydroxyethyl cellulose used has a hydroxyethyl M.S. of 3.5, and 0.9% of a $C_{12}$ hydrocarbon radical substitution. The resulting toothpaste has a yield value of 3500 dyne/cm² at a shear rate of 1.8 sec$^{-1}$, good body characteristics, and short texture.

Thus, this invention provides a novel transparent dentifrice composition or gel toothpaste having excellent body characteristics upon storage and upon extrusion from the tube, and a distinct lack of stringiness or very short texture upon breaking from the tube.

Features, advantages and other specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. A transparent dentifrice composition consisting essentially of:
    (a) a mixture containing from about 80% to about 90% of a humectant and from about 10% to about 20% of a suitable vehicle for the humectant;
    (b) from about 5% to about 50% of a finely divided dental abrasive;
    (c) from about 1% to about 10% of a silica thickener; and
    (d) from about 0.1% to about 0.4% of a hydrophobically modified hydroxyethyl cellulose which is hydrophobically modified with a hydrocarbon radical having 8 to 25 carbon atoms and which has a hydroxyethyl M.S. of from about 2.5 to about 3.5.

2. The composition of claim 1 wherein the hydrocarbon radical is present in an amount from about 0.1 to about 0.9%.

3. The composition of claim 1 wherein the humectant is selected from the group consisting of glycerin, sorbitol, propylene glycol and mixtures thereof.

4. The composition of claim 1 wherein a suitable vehicle for the humectant is water.

5. The composition of claim 1 wherein the finely divided dental abrasive is a high silica content material of at least 70% silica.

6. The composition of claim 5 wherein the silica has a particle size from about 2 to about 20 microns, and a refractive index which is substantially the same as the humectant and vehicle mixture.

7. The composition of claim 1 wherein the silica thickener is selected from the group consisting of silica aerogel, dehydrated silica hydrogel, precipitated silica, and pyrogenic silica.

8. The composition of claim 1 wherein the hydrophobically modified hydroxyethyl cellulose is present in an amount from about 0.2% to about 0.3%.

9. The composition of claim 1 which further comprises a polyethylene glycol having a molecular weight of from about 300 to about 20,000.

10. The composition of claim 9 wherein the polyethylene glycol is present in an amount of 1% to about 5%.

* * * * *